United States Patent [19]
Thompson

[11] Patent Number: 5,474,664
[45] Date of Patent: Dec. 12, 1995

[54] CLEANING OF SENSOR SURFACES

[75] Inventor: Huvin Thompson, Slimbridge, United Kingdom

[73] Assignee: ABB Kent Plc, Bedfordshire, England

[21] Appl. No.: 11,206

[22] Filed: Jan. 26, 1993

[30] Foreign Application Priority Data

Jan. 29, 1992 [GB] United Kingdom ............ 9201886

[51] Int. Cl.$^6$ .................................................. G01N 27/38
[52] U.S. Cl. ................ 204/402; 204/153.1; 204/400
[58] Field of Search .................................... 204/400, 402, 204/153.1; 15/159.1, 160

[56] References Cited

U.S. PATENT DOCUMENTS

| | | | |
|---|---|---|---|
| 878,344 | 2/1908 | Chazal | 15/159.1 |
| 1,120,476 | 12/1914 | Hansen | 15/160 |
| 1,617,569 | 2/1927 | Boyle | 15/159.1 |
| 1,967,593 | 7/1934 | Saladow | 15/159.1 |
| 2,414,411 | 1/1947 | Marks | 204/402 |
| 3,216,915 | 11/1965 | Arthur et al. | 204/402 |
| 4,285,792 | 8/1981 | McGandy | 204/402 |

FOREIGN PATENT DOCUMENTS 0012893  1/1977  Japan ................ 204/402

*Primary Examiner*—T. Tung
*Attorney, Agent, or Firm*—Hodgson, Russ, Andrews, Woods & Goodyear

[57] ABSTRACT

In a sensor such as a pH sensor, a bundle of relatively long, thin and soft cleaning filaments is anchored next to the pH electrode. A bluff body, which may be the reference electrode is positioned upstream of the bundle so as to create liquid vortices which move the free ends of the fibres in an effective cleaning action over the sensing surface of the pH electrode.

29 Claims, 2 Drawing Sheets

CLEANING OF SENSOR SURFACES

FIELD OF THE INVENTION

This invention relates to arrangements for maintaining the cleanliness of sensor surfaces, particularly such surfaces which are in contact with flowing liquid. One example is the use of sensors to monitor pH in flowing water.

BACKGROUND OF THE INVENTION

It is essential in monitoring pH that the sensor, usually a glass electrode, does not become so fouled as to prevent the sensor surface being in direct contact with the sample. With a glass electrode, or other potentiometric sensor, a substantial area of the sensor surface must be free of fouling.

It is found that fouling of a reference electrode junction, unless exceptionally heavy, rarely leads to a significant problem. However, even mild fouling of a glass electrode can quickly result in a sluggish response to changing sample pH and eventually to a complete lack of response. Such behaviour can occur relatively rapidly, often within a few hours. It is therefore not possible to deal with the problem in any sensible cleaning/maintenance schedule.

It will be appreciated that these observations apply to a wide variety of electrometric measurements that rely on direct contact between a sensor surface and a sample. Related problems may also arise with other forms of sensor surface such as a window provided for an optical sensing measurement.

Manufacturers of sensors have hitherto offered a variety of so-called electrode cleaners. This term is generally a misnomer as the use of many of these devices is aimed at preventing or reducing fouling. These "cleaners" may be roughly classified into three main groups: ultrasonic, mechanical and chemical.

Ultrasonic devices are usually excellent in preventing crystallization from a liquid sample onto the electrode surface (for example calcium sulphate in water treatment plant); in maintaining light oils and solvents in aqueous suspension and in reducing the slow deposition of fine flocculants. The basis of the technique is of high frequency vibrations generated from an emitter, causing cavitation at the electrode surface preventing or removing depositions. The disadvantage of the ultrasonic approach is principally that of cost.

A typical known mechanical cleaner takes the form of a brush moving across or around the sensor surface driven externally, either electrically or with compressed air. The individual bristles of the brush are commonly of plastic and are stiff. Generally they are ineffective against oil or grease contaminants or where crystallization may occur and are not recommended where the sample may contain abrasive matter which would damage the sensor surface. An alternative approach is suggested in DE 1217656 which shows a frame rotated about the bulb of a pH electrode, the frame carrying stretched elastic strips which rub over the bulb surface. An expensive drive arrangement is required to rotate the frame.

With reference to U.S. Pat. No. 4,285,792, there has been proposed a paddle wheel driven by the flow of sample liquid and carrying bristle cleaning brushes which sweep over the surface of a pH electrode. Whilst the expense of a separate drive arrangement is in this way avoided, the rotatable paddle wheel represents a mechanical complexity in the measurement cell and operation can only be guaranteed at relatively high flow velocities. Further alternative proposals for a mechanical cleaner utilise the motion of plastic (PTFE) balls or a foamed plastic body (see DE 3405234) captured within a suitable housing around the sensor surface and powered by the sample flow physically to prevent accumulation of coating materials on the sensor surface. Significant flow rates are recommended to maintain sufficient motion of the plastic balls and the arrangement of course requires a chamber surrounding the sensor, to contain the balls or other body.

Unlike mechanical and ultrasonic "cleaners" which do not interfere with the measurement and maybe continuously operated, chemical cleaners have the disadvantage of requiring system isolation from the sample stream during the cleaning cycle. This usually entails the provision of bypass lines, valves and perhaps a drain to waste. They comprise a jet or ring of jets directed at the sensor surface. On activation, reagent is under electrical power pumped via the jets onto the sensor surface.

SUMMARY OF THE INVENTION

It is an object of this invention to provide a sensor having an improved arrangement for maintaining cleanliness of a sensor surface which does not add significantly to the cost of the sensor and which is effective against a range of contaminants, interferents or fouling agents.

It is a further object of this invention to provide an improved method of maintaining the cleanliness of a sensing surface which is inexpensive in operation and effective against a range of continents or fouling agents.

It is yet a further object of this invention to provide an improved method of maintaining the cleanliness of a sensing surface which is capable of operating in both flow chamber and probe sensing arrangements.

It is still a further object of this invention to provide an improved sensor surface cleaning element.

Accordingly, the present invention consists, in one aspect, in a sensor for determining parameters of a flowing liquid, comprising a flow chamber having an inlet port and and outlet port; a sensing element positioned in the flow chamber and having a sensor surface which in use contacts liquid flowing through the flow chamber and cleaning means for maintaining the cleanliness of the sensor surface, wherein said cleaning means comprises a plurality of cleaning filaments anchored at respective first ends in fixed position relative to said sensor surface and movable at respective second ends by the action of turbulence in the flowing liquid, said movement of the respective second ends of the filaments providing a cleaning action over at least part of the sensor surface.

Preferably, there is provided a bluff body positioned in the flow chamber generally upstream of the cleaning filaments and serving in use to shed liquid vortices capable of moving the cleaning filaments at their respective second ends.

In a further aspect, the present invention consists in a sensor for determining parameters of a flowing liquid, in the form of a probe insertable in a liquid flow path, the sensor comprising a sensing element positionable in the liquid flow and having a sensor surface which in use contacts flowing liquid and cleaning means for maintaining the cleanliness of the sensor surface, wherein said cleaning means comprises a plurality of cleaning filaments anchored at respective first ends in fixed position relative to said sensor surfaces and movable at respective second ends by the action of turbulence in the flowing liquid, said movement of the respective second ends of the filaments providing a cleaning action over at least part of the sensor surface.

In still a further aspect, the present invention consists in a method for maintaining the cleanliness of the sensing surface of an electrometric sensor, which sensing surface is positioned in a flow of liquid, comprising the steps of providing in generally fixed relation to the sensing surface a bundle of cleaning filaments, a substantial number of the cleaning filaments contacting the sensing surface at respective free ends thereof; and providing in the region of the cleaning filaments a degree of liquid flow turbulence which is sufficient having regard to the length, thickness and material of the cleaning filaments, to cause the free ends of the cleaning filaments to move in effective cleaning action over the sensing surface.

In yet a further aspect, the present invention consists in a sensor surface cleaning element for use with a sensor having a sensing surface contacted in operation by a flow of liquid, the cleaning element comprising an anchorage positionable in fixed relation to the sensing surface and a plurality of cleaning filaments having respective first ends secured to the anchorage and respective second ends free to move in operation in cleaning action over the sensing surface, each filament having a length to thickness ratio of at least 500:1.

It has surprisingly been found that a body of cleaning elements which are capable of being moved at their free ends by vortices or other turbulance in the flowing liquid, can be effective against a range of fouling agents.

Arrangements according to the present invention have the merit of mechanical simplicity, requiring no moving parts beyond the filaments themselves. Use of the present invention is not constrained to flow chamber sensing geometries; effective cleaning action can be provided in a probe sensor. Still further advantages of the present invention will become apparent in the following detailed description.

DETAILED DESCRIPTION OF PREFERRED EMBODIMENTS

Figure 1:
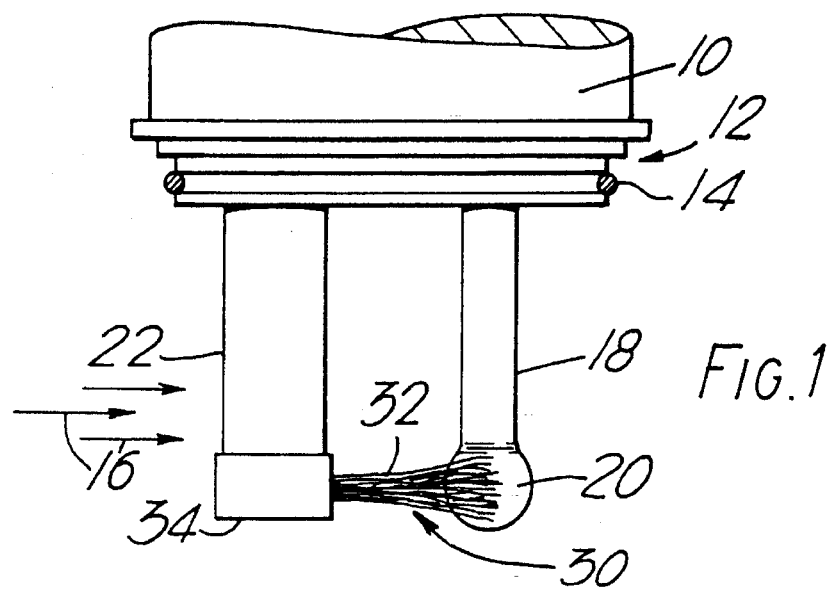
FIG. 1 is a side view of a pH sensor arrangement in accordance with this invention.
Figure 2:
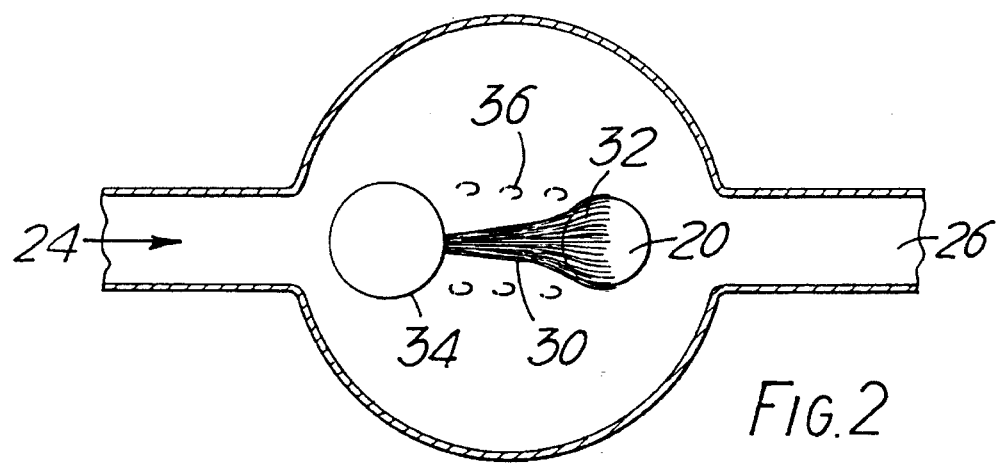
FIG. 2 is a somewhat diagrammatic under plan view of the pH sensor shown in FIG. 1.

Referring to FIGS. 1 and 2, there is shown a sensor having a cylindrical body 10 provided with a mounting flange 12 and O-ring seal 14 for mounting either in a flow cell or a probe arrangement. In either case, there will be a flow of liquid past the sensor in the direction shown by the arrows 16.

A pH glass electrode 18 projects from the body 10 into the liquid flow. The pH electrode may take a variety of forms and will typically have a glass bulb 20. A reference electrode 22 is similarly mounted in the body 10 and may again take a variety of standard forms.

In the case where the pH sensor is provided in a flow cell, the reference electrode 22 will be positioned adjaced the inlet port 24 as seen in FIG. 2. There is an in-line outlet port 26 also shown.

To maintain the cleanliness of the glass bulb 20, or at least a substantial proportion of the surface of the bulb 20, there is provided a cleaning element 30. This takes the form of a large number of soft polyamide fibres 32 of diameter around 0.01 mm. The body of fibres has an overall thickness of around 10 mm and the individual fibres are approximately 20 mm in length. The body of fibres 32 is mounted in a sleeve 34 which is conveniently mounted on the reference electrode 22.

The principle of operation of the device is that fluid vortices (indicated in FIG. 2 at 36) serve to move the fibres 32 over the surface of the bulb 20. The generation of vortices is ensured by arranging that the free ends of the fibres lie downstream in the flow from a bluff body, in this case the reference electrode 22 and mounting sleeve 34. The rate of generation of vortices and the optimum separation in the direction flow, between the bluff body and the fibre ends, can be calculated from the dimensions of a bluff body and the flow parameters. It is found that effective cleaning action can be achieved at relatively low flow rates; in one specific example motion of the fibres was observed at flow rates as low as 5 $dm^3$/min.

It is believed that the mass of fine fibres surrounding the upstream surface of the pH bulb 20 may serve an additional function of filtering particulate fouling material. The envelope of fibres might thus serve directly to protect the sensor surface from the worst effects of material fouling whilst remaining unclogged itself by virtue of the continuous movement of the individual fibres. This masking effect of the envelope is, however, insufficient to stop the liquid sample from properly contacting the sensor surface.

In one experiment, the described sensor arrangement was exposed to a water flow containing a suspension of ferric hydroxide. After a period of around 20 hours at flow rates of typically 15 $dm^3$/min, visual examination of the pH electrode indicated that the portion of the electrode in contact with the moving fibres was clear of fouling whilst that portion which was not in contact was heavily fouled.

It would be understood that the brush element could take a variety of forms beyond that illustrated in the drawings. Thus the length of the fibres could be altered, either maintaining a uniform length or, in a further modification, varying the length between the fibres so as to produce a profile at the free end which conforms with that of the sensor surface. The thickness of the fibres may similarly be varied. It being important that the length, thickness and flexibility of the fibre is selected so that the free end is capable of being driven in cleaning action by vortices generated in the anticipated flow rate. It is believed to be important that the length of each fibre or filament is very much greater than its diameter, in a ratio which is suitably at least 100:1; preferably at least 500:1 and advantageously at least 1000:1. The inherent flexibility of the material is of course a further relevant parameter. It will be understood that a variety of materials can be used for the fibres, a useful alternative to the described polyamide being polypropylene. Still further alternative materials are polyester, acrylic, viscose and cellulosic fibres including appropriate natural fibres. The chosen material must of course provide the necessary degree of flexibility as well as being inert to the particular sample.

Figure 3:
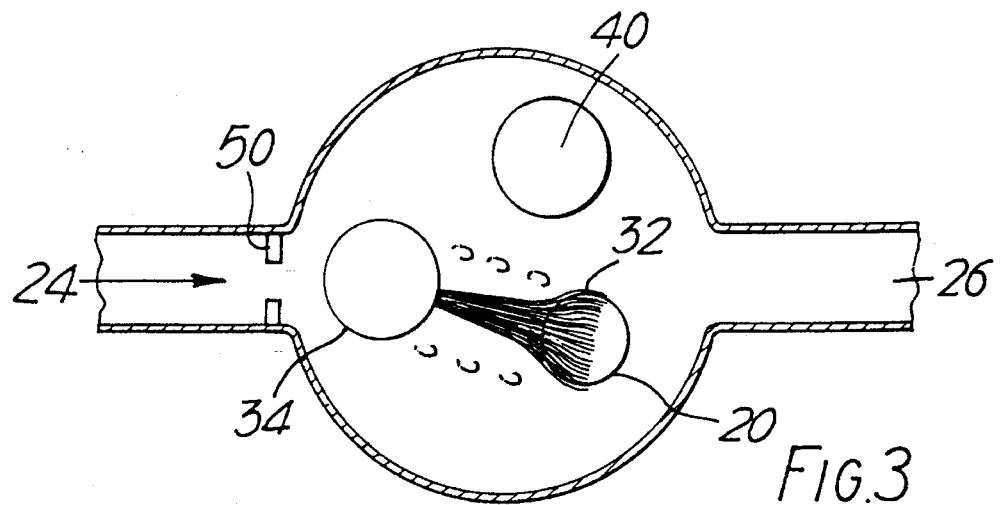
FIG. 3 is a view similar to FIG. 2 illustrating two modifications.

A typical pH sensor may include a temperature compensator in addition to the described pH electrode and reference electrode. This necessitates a modified geometry as shown in FIG. 3. The reference electrode 22 remains adjacent the inlet port 24, but the pH electrode 18, 20 is offset to accommodate a temperature compensator 40. The filament mounting sleeve is rotated relatively to the reference electrode so that the cleaning filaments 32 remain directed toward the pH bulb 20.

Whilst, in this embodiment the bluff body—in the form of the reference electrode 22—remains in direct line with the inlet port 24, this is not found to be an essential requirement. The position of the bluff body may within limits be varied, both in the direction of the incoming flow and also transverse to that direction, while still producing a sufficient degree of turbulence to move the cleaning filaments.

Whilst it is convenient to mount the brush element on the reference electrode and to use the reference electrode as a bluff body shedding the required vortices, other alternatives are possible. Thus a bluff body of optimum dimension and profile could be provided as a separate component. That bluff body could conveniently form a mounting for the fibre elements but need not necessarily do so. It will be possible, for example, for the fibre elements to be anchored to an appropriate support on the pH electrode. The fibres need not be parallel to the flow direction provided that the free ends of the fibres are capable of being moved in cleaning action over the sensor surface by the flowing liquid. The body of fibre elements may itself take other form being, for example, in a "flag" or planar configuration.

It is recognised that the frequency at which vertices are shed by a bluff body in a liquid flow, will increase with increases in flow velocity. Accordingly, to reduce the minimum flow rate at which a particular arrangement of filaments will provide adequate cleaning action, it is proposed to introduce a restrictor or throttle to increase flow velocity.

Referring again to FIG. 3, there is shown in the inlet port 24, an orifice plate 50. This serves to reduce the diameter of the inlet port, in one example, from 30 mm to 10 mm. For a particular flow rate through the cell, the flow velocity is accordingly increased. This in turn leads to an increase in the frequency at which vortices are shed. The practical advantage is that, in this example, the minimum flow rate at which satisfactory cleaning is assured, is reduced from about 5 to about 2 dm$^3$/min.

In a further modification the vertices or other turbulence in the flowing liquid serving to move the fibres in cleaning action may be generated not by a bluff body upstream of the fibre ends but by some other component in the flow path. It is anticipated, for example, that an aperture serving as the inlet to a flow cell may under appropriate flow conditions generate vertices or other turbulence sufficient to move the fibre ends in cleaning action.

Figure 4:
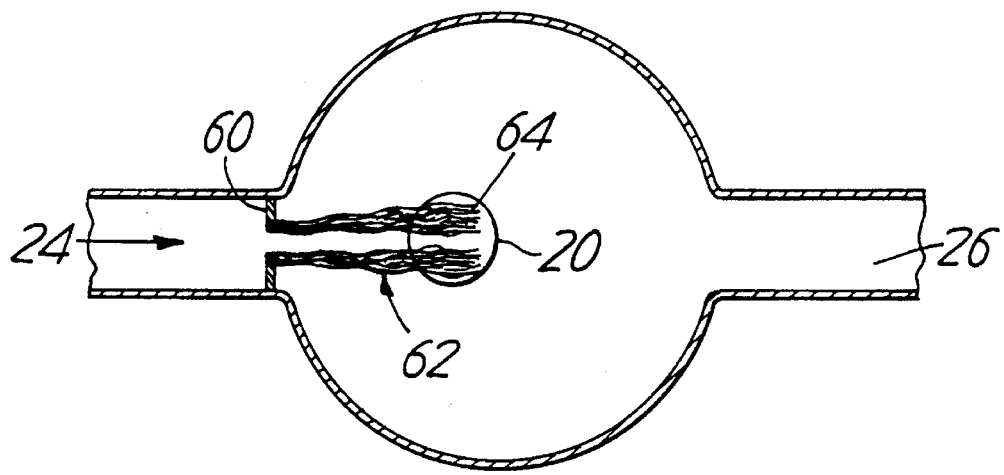
FIG. 4 is a view similar to FIG. 2 illustrating a still further modification.
Figure 5:
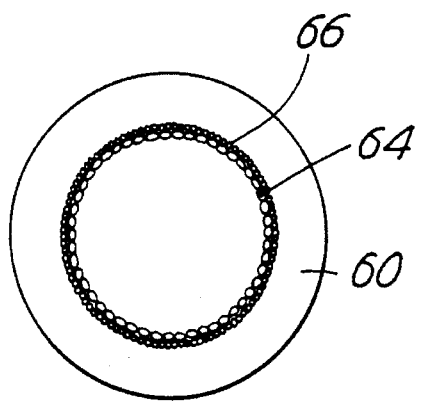
FIG. 5 is an end view of an orifice plate for use in the arrangement of FIG. 4 (to an enlarged scale)
Figure 6:
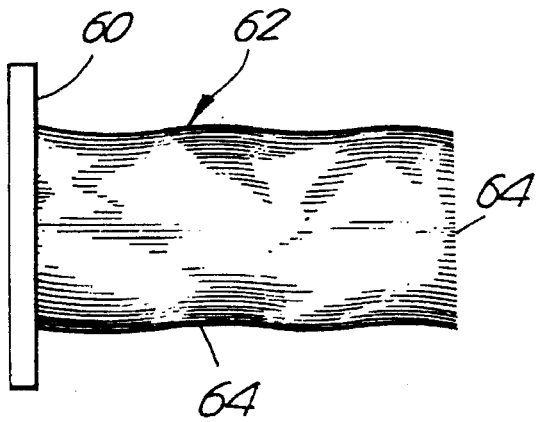
FIG. 6 is a side view of the orifice plate of FIG. 5.

It is possible to combine this feature with the use of an orifice plate as previously described. Thus, referring for example to FIG. 4, there is shown an orifice plate 60 carrying a cylindrical shroud 62 of cleaning filaments 64. As seen more clearly in FIGS. 5 and 6, the inner circular edge 66 of the annular orifice plate 60 provides an anchorage for the fixed ends of the filaments 64. This may be bonded to the edge 66 with an epoxy or other suitable adhesive.

It should be recognised that although this invention has been described with the example of pH electrodes, it has wider application to other potentiometric sensors, to electometric sensors broadly and to a still wider variety of sensors having a sensor surface in contact with a sample flow and liable to fouling. The sensor surface could, in one variation, comprise an optical window through which laser based or other optical measurements are taken of sample parameters.

The contaminents or fouling agents which are removed or avoided through use of the present invention will similarly vary widely and will include precipitating agents, hydrophopic suspensions and a range of solid debris. In certain cases, the present invention will be effective in removing or dislodging air or other gas bubbles which would otherwise interfere with sensor operation. Whilst the examples in this description have been chosen from aqueous flows, the invention is applicable with appropriate sensors to other liquid environments.

I claim:

1. A sensor for determining parameters of a flowing liquid, comprising a flow chamber having an inlet port and outlet port; a sensing element positioned in the flow chamber and having a sensor surface which in use contacts liquid flowing through the flow chamber and cleaning means for maintaining the cleanliness of the sensor surface, wherein said cleaning means comprises a plurality of cleaning filaments anchored at respective first ends in fixed position relative to said sensor surface and movable at respective second ends by the action of turbulence in the flowing liquid acting on said second ends, said movement of the respective second ends of the filaments providing a cleaning action over at least part of the sensor surface.

2. A sensor according to claim 1, further comprising a bluff body positioned in the flow chamber generally upstream of the cleaning filaments and serving in use to generate liquid vortices capable of moving the cleaning filaments at their respective second ends.

3. A sensor according to claim 2, wherein the cleaning filaments are anchored at respective first ends thereof to the bluff body.

4. A sensor according to claim 3, wherein said sensing element comprises a first sensing element, wherein said sensor further includes a second sensing element, and wherein the second sensing element serves as the bluff body in relation to the movement of cleaning filaments over the sensor surface of the first sensing element.

5. A sensor according to claim 2, wherein said sensing element comprises a first sensing element, wherein said sensor further includes a second sensing element, and wherein the second sensing element serves as the bluff body in relation to the movement of cleaning filaments over the sensor surface of the first sensing element.

6. A sensor according to claim 1, further comprising throttle means positioned in relation to the inlet port and serving to increase liquid flow velocity.

7. A sensor according to claim 6, wherein the throttle means comprises an orifice plate.

8. A sensor according to claim 7, wherein said respective first ends of the cleaning filaments are anchored to the orifice plate.

9. A sensor according to claim 8, wherein the cleaning filaments are arranged in a cylindrical shroud.

10. A sensor according to claim 1, wherein the cleaning filaments are arranged in a cylindrical shroud.

11. A sensor according to claim 1, in which each cleaning filament has a length to thickness of ratio of at least 100:1.

12. A sensor according to claim 11, in which each cleaning filament has a length to thickness ratio of at least 500:1.

13. A sensor according to claim 12, in which each cleaning filament has a length to thickness ratio of at least 1000:1.

14. A sensor for determining parameters of a flowing liquid, in the form of a probe which in use is inserted in a liquid flow path, the sensor comprising; a sensing element which in use is positioned in the liquid flow path and having a sensor surface which in use contacts the flowing liquid and cleaning means for maintaining the cleanliness of the sensor surface, wherein said cleaning means comprises a plurality of cleaning filaments anchored at respective first ends in fixed position relative to said sensor surface and movable at respective second ends by the action of turbulence in the flowing liquid acting on said second ends, said movement of the respective second ends of the filaments providing a cleaning action over at least part of the sensor surface.

15. A sensor according to claim 14, further comprising a bluff body positioned generally upstream of the cleaning filaments in the liquid flow path and serving in use to generate liquid vortices capable of moving the cleaning filaments at their respective second ends.

16. A sensor according to claim 15, wherein the cleaning filaments are anchored at respective first ends thereof to the bluff body.

17. A sensor according to claim 16, wherein said sensing element comprises a first sensing element, wherein said sensor further includes a second sensing element, and wherein the second sensing element serves as the bluff body in relation to the movement of cleaning filaments over the sensor surface of the first sensing element.

18. A sensor according to claim 15, wherein said sensing element comprises a first sensing element, wherein said sensor further includes a second sensing element, and wherein the second sensing element serves as the bluff body in relation to the movement of cleaning filaments over the sensor surface of the first sensing element.

19. A sensor according to claim 15, further comprising throttle means positionable in the liquid flow in relation to the bluff body serving to increase liquid flow velocity in the region of the bluff body and thereby to increase the frequency at which vortices are generated.

20. A sensor according to claim 19, wherein the throttle means comprises an orifice plate.

21. A sensor according to claim 20, wherein said respective first ends of the cleaning filaments are anchored to the orifice plate.

22. A sensor according to claim 21, wherein the cleaning filaments are arranged in a cylindrical shroud.

23. A sensor according to claim 14, wherein the cleaning filaments are arranged in a cylindrical shroud.

24. A sensor according to claim 14, in which each cleaning filament has a length to thickness ratio of at least 100:1.

25. A sensor according to claim 24, in which each cleaning filament has a length to thickness ratio of at least 500:1.

26. A sensor according to claim 25, in which each cleaning filament has a length to thickness ratio of at least 1000:1.

27. A sensor for determining flow parameters of a liquid in combination with a sensor surface cleaning element, the sensor having a sensing surface contacted in operation by a flow of liquid, the cleaning element comprising an anchorage positionable in fixed relation to the sensing surface and a plurality of cleaning filaments having respective first ends secured to the anchorage and respective second ends free to move in operation in cleaning action over the sensing surface, said second ends being moved by the action of turbulence in the flow of liquid acting on said second ends, each filament having a length to thickness ratio of at least 500:1.

28. A sensor according in claim 27, wherein said anchorage comprising a sleeve for mounting upon a reference element positioned adjacent said sensor.

29. A sensor according to claim 28, wherein said anchorage comprises an annulus locatable in an inlet port of a sensing chamber.

\* \* \* \* \*